United States Patent
Takada et al.

(10) Patent No.: US 11,749,011 B2
(45) Date of Patent: Sep. 5, 2023

(54) DETECTING DEVICE

(71) Applicant: Japan Display Inc., Tokyo (JP)

(72) Inventors: Sabu Takada, Tokyo (JP); Yoshihiro Kotani, Tokyo (JP)

(73) Assignee: Japan Display Inc., Tokyo (JP)

( * ) Notice: Subject to any disclaimer, the term of this patent is extended or adjusted under 35 U.S.C. 154(b) by 46 days.

(21) Appl. No.: 17/670,659

(22) Filed: Feb. 14, 2022

(65) Prior Publication Data

US 2022/0165080 A1 May 26, 2022

Related U.S. Application Data

(63) Continuation of application No. PCT/JP2020/031334, filed on Aug. 19, 2020.

(30) Foreign Application Priority Data

Sep. 3, 2019 (JP) .................................. 2019-160420

(51) Int. Cl.
*G06V 40/13* (2022.01)
*G06V 40/12* (2022.01)

(52) U.S. Cl.
CPC ...... *G06V 40/1306* (2022.01); *G06V 40/1365* (2022.01)

(58) Field of Classification Search
CPC ............ G06V 40/1306; G06V 40/1365; A61B 5/1172; G06F 3/041; G06F 3/044; G06T 1/00
See application file for complete search history.

(56) References Cited

U.S. PATENT DOCUMENTS

2006/0158202 A1 7/2006 Umeda et al.
2012/0262389 A1 10/2012 Kida et al.
(Continued)

FOREIGN PATENT DOCUMENTS

JP 2005-152223 A 6/2005
JP 2012-221422 A 11/2012
(Continued)

OTHER PUBLICATIONS

Search Report issued in International Patent Application No. PCT/JP2020/031334 dated Nov. 17, 2020 and English translation of same. 5 pages.
(Continued)

*Primary Examiner* — Edward F Urban
*Assistant Examiner* — Wassim Mahrouka
(74) *Attorney, Agent, or Firm* — K&L Gates LLP

(57) ABSTRACT

A detecting device includes a substrate, a plurality of detection electrodes provided on the substrate and arrayed in a first direction parallel to the substrate, a plurality of drive electrodes provided on the substrate and arrayed in a second direction intersecting the first direction, a second selection circuit configured to select a plurality of the detection electrodes based on selection signals, a first selection circuit configured to select a plurality of the drive electrodes, a detector coupled to the selected detection electrodes out of the detection electrodes, and a memory storing therein, as a set of output data, a plurality of detection signals output from the selected detection electrodes via the detector by the first selection circuit scanning the drive electrodes in one period when the second selection circuit selects the detection electrodes.

6 Claims, 11 Drawing Sheets

(56) References Cited

U.S. PATENT DOCUMENTS

2013/0321382 A1* 12/2013 Nagao ................... G06F 1/3262
                                                              345/212
2015/0185927 A1    7/2015 Inoue et al.
2019/0377471 A1* 12/2019 Kitagawa ............ G06F 3/04184

FOREIGN PATENT DOCUMENTS

JP     2019-125072 A      7/2019
WO    WO2014/061261 A1    4/2014
WO    WO-2019138621 A1 *  7/2019

OTHER PUBLICATIONS

Written Opinion issued in International Patent Application No. PCT/JP2020/031334 dated Nov. 17, 2020. 4 pages.

* cited by examiner

DETECTING DEVICE

CROSS-REFERENCE TO RELATED APPLICATION

This application is a continuation of International Patent Application No. PCT/JP2020/031334 filed on Aug. 19, 2020 which designates the United States, incorporated herein by reference, and which claims the benefit of priority from Japanese Patent Application No. 2019-160420 filed on Sep. 3, 2019, incorporated herein by reference.

BACKGROUND

1. Technical Field

The present disclosure relates to a detecting device.

2. Description of the Related Art

Fingerprint sensors detect the shape of a fingerprint of a finger in contact with a detection surface by detecting a change in capacitance due to recesses and protrusions of the fingerprint (e.g., Japanese Patent Application Laid-open Publication No. 2005-152223 (JP-A-2005-152223)). Results of detection performed by the fingerprint sensors are used for personal authentication, for example. In the fingerprint sensor described in JP-A-2005-152223, a plurality of row wires and a plurality of column wires are disposed intersecting each other. The column wires are driven based on a code having the number of bits corresponding to the number of column wires.

The fingerprint sensor described in JP-A-2005-152223 switches coupling of a selector coupled to the row wires in a period when the column wires are driven by a single code. In addition, the fingerprint sensor switches coupling of the selector in each period when the column wires are driven by different codes. In other words, the fingerprint sensor detects detection signals from the row wires in all the periods corresponding to the number of bits of the code and stores the detection signals of one frame in a memory. As a result, the capacity of the memory may possibly increase.

An object of the present disclosure is to provide a detecting device that can suppress an increase in capacity of a memory.

SUMMARY

A detecting device according to an embodiment of the present disclosure includes a substrate, a plurality of detection electrodes provided on the substrate and arrayed in a first direction parallel to the substrate, a plurality of drive electrodes provided on the substrate and arrayed in a second direction intersecting the first direction, a second selection circuit configured to select a plurality of the detection electrodes based on selection signals, a first selection circuit configured to select a plurality of the drive electrodes, a detector coupled to the selected detection electrodes out of the detection electrodes, and a memory storing therein, as a set of output data, a plurality of detection signals output from the selected detection electrodes via the detector by the first selection circuit scanning the drive electrodes in one period when the second selection circuit selects the detection electrodes.

DETAILED DESCRIPTION

Figure 1:
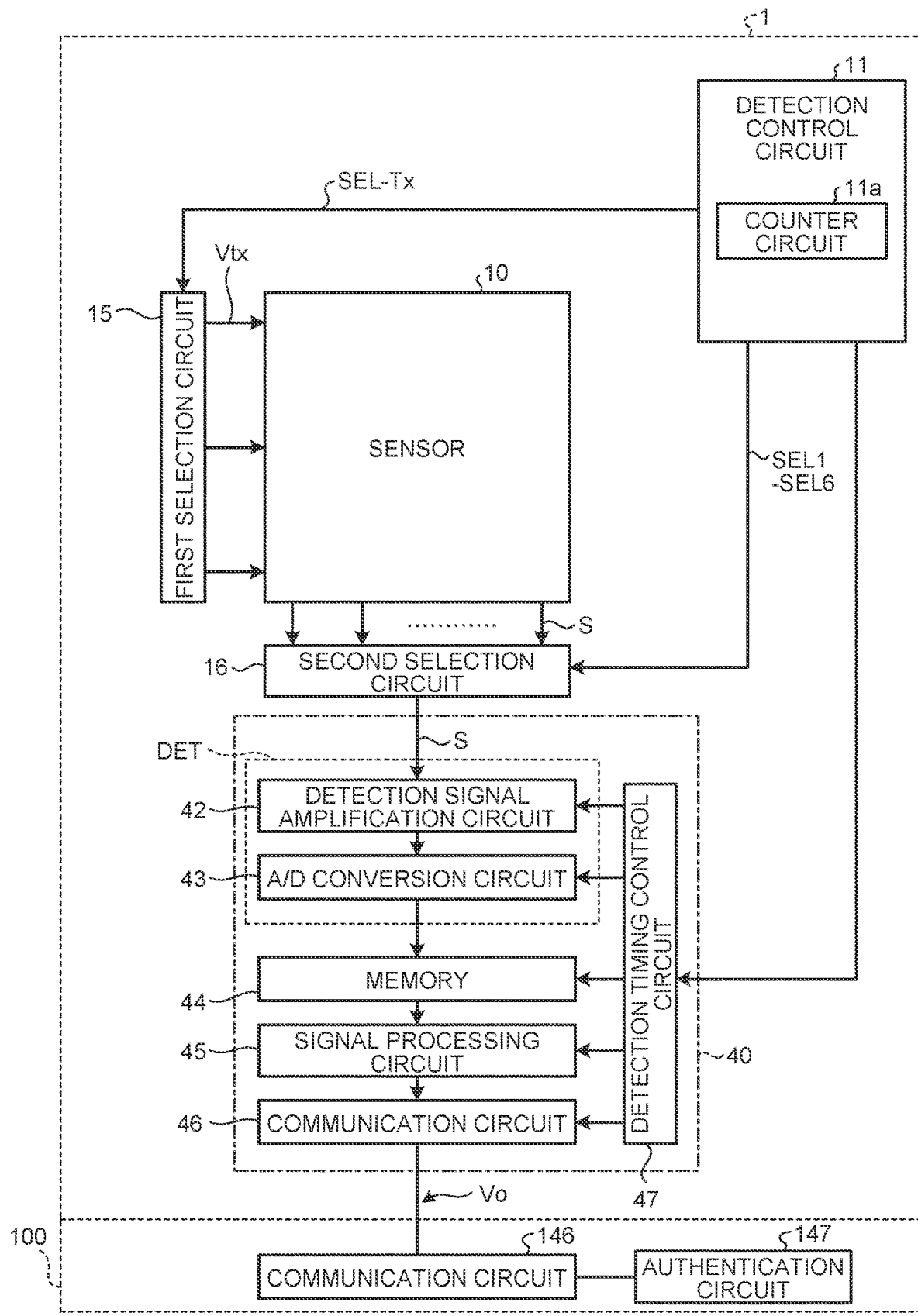
FIG. 1 is a block diagram of an example of the configuration of a detecting device according to an embodiment.

Exemplary aspects (embodiments) to embody the present disclosure are described below in greater detail with reference to the accompanying drawings. The contents described in the embodiments are not intended to limit the present disclosure. Components described below include components easily conceivable by those skilled in the art and components substantially identical therewith. Furthermore, the components described below may be appropriately combined. What is disclosed herein is given by way of example only, and appropriate modifications made without departing from the spirit of the present disclosure and easily conceivable by those skilled in the art naturally fall within the scope of the disclosure. To make the explanation more specific, the drawings may possibly illustrate the width, the thickness, the shape, and other elements of each component more schematically than the actual aspect. These elements, however, are given by way of example only and are not intended to limit interpretation of the present disclosure. In the present specification and the figures, components similar to those previously described with reference to previous figures are denoted by like reference numerals, and detailed explanation thereof may be appropriately omitted.

Embodiments

FIG. 1 is a block diagram of an example of the configuration of a detecting device according to an embodiment. As illustrated in FIG. 1, a detecting device 1 includes a sensor 10, a detection control circuit 11, a first selection circuit 15, a second selection circuit 16, and a detection circuit 40.

The detecting device 1 is a fingerprint detecting device that detects a fingerprint by detecting information on recesses and protrusions on the surface of an object to be detected (e.g., a finger) in contact with or in proximity to the sensor 10 by a capacitive system. The object to be detected is not limited to a finger and may be any desired object as long as it changes capacitance formed with at least one of detection electrodes Rx and drive electrodes Tx due to the recesses and protrusions on the surface. The object to be detected may be a palm print, for example. The sensor 10 has a detection region FA provided with a plurality of sensor elements SE. The sensor element SE outputs detection signals S corresponding to the position of the sensor element SE in the detection region FA and the recesses and protrusions on the surface of the object to be detected. The sensor element SE is composed of a detection electrode Rx and a drive electrode Tx, and more specifically is an intersection of the detection electrode Rx and the drive electrode Tx.

The detection control circuit 11 controls detection operations performed by the sensor 10. Specifically, the detection control circuit 11 includes a counter circuit 11a. The counter circuit 11a measures pulses of clock signals of the detection control circuit 11. The counter circuit 11a generates timing control signals for controlling a timing for selecting the drive electrode Tx and the detection electrode Rx based on the measured value of the number of pulses. The detection control circuit 11 supplies control signals to the first selection circuit 15, the second selection circuit 16, and the detection circuit 40 based on the timing control signals supplied from the counter circuit 11a and controls the operations performed by these circuits.

The first selection circuit 15 (drive electrode selection circuit) is a switch circuit (multiplexer) that selects the drive electrode Tx based on selection signals SELy supplied from the detection control circuit 11. The selection signal SELy is a signal based on a predetermined code. In other words, the first selection circuit 15 selects the sensor elements SE arrayed in a second direction Dy based on the selection signals SELy corresponding to the predetermined code. The predetermined code is based on a square matrix the elements of which are either "1" or "−1" or either "1" or "0" and two desired different rows of which are an orthogonal matrix. The predetermined code is based on a Hadamard matrix, for example. The first selection circuit 15 for the first row, for example, associates the row or the column of the Hadamard matrix with the position of the drive electrode Tx in a first direction Dx. The first selection circuit 15 supplies drive signals Vtx to the drive electrode Tx selected based on "1" or "−1" included in each column or row. The drive signal Vtx is an alternating-current (AC) square wave at a predetermined frequency (e.g., a frequency of the order of several kilohertz to several hundred kilohertz), for example. The AC square wave of the drive signals Vtx may be a sine wave or a triangle wave.

The second selection circuit 16 (detection electrode selection circuit) is a switch circuit (multiplexer) that selects the detection electrode Rx based on selection signals SELx (SELx1 to SELx6) supplied from the detection control circuit 11. The second selection circuit 16 couples the selected detection electrode Rx to the detection circuit 40. The second selection circuit 16 outputs detection signals S received from the selected detection electrode Rx to the detection circuit 40. In other words, a plurality of detection elements SE corresponding to a plurality of rows selected by the first selection circuit 15 based on the selection signals SELy and to a plurality of columns selected by the second selection circuit 16 based on the selection signals SELx are coupled to the detection circuit 40. An integrated value of detection signals Si of the detection elements SE selected based on the selection signals SELy and the selection signals SELx is output as the detection signal S.

The detection circuit 40 detects the shape of a finger and a fingerprint based on the control signals supplied from the detection control circuit 11 and the detection signals S supplied from the sensor 10. The detection circuit 40, for example, detects a change in the detection signals S due to the recesses and protrusions on the surface of a finger or the like in contact with or in proximity to the sensor 10.

The detection circuit 40 includes a detection signal amplification circuit 42, an A/D conversion circuit 43, a memory 44, a signal processing circuit 45, a communication circuit 46, and a detection timing control circuit 47. The detection timing control circuit 47 controls the detection signal amplification circuit 42, the A/D conversion circuit 43, the memory 44, the signal processing circuit 45, and the communication circuit 46 such that they operate synchronously with one another based on the control signals supplied from the detection control circuit 11.

The detection signal amplification circuit 42 amplifies the detection signals S. The detection signal amplification circuit 42 includes a plurality of integration circuits and terminals coupled to the respective integration circuits, for example. The second selection circuit 16 couples the terminal of the detection signal amplification circuit 42 to the selected detection electrode Rx. The A/D conversion circuit 43 converts analog signals output from the detection signal amplification circuit 42 into digital signals. A detector DET includes the detection signal amplification circuit 42 and the A/D conversion circuit 43. The detection signal amplification circuit 42 and the A/D conversion circuit 43 are analog front end (AFE) circuits, for example.

The memory 44 is a storage circuit that stores therein a plurality of detection signals S output from a plurality of selected detection electrodes Rx of the sensor 10 via the detector DET as a set of output data RD. The memory 44 may be a random access memory (RAM) or a register circuit, for example. The output data RD is also called raw data to be subjected to signal processing by the signal processing circuit 45.

The signal processing circuit 45 receives the output data RD as raw data from the memory 44 and performs signal processing on the output data RD. The signal processing circuit 45, for example, performs sorting or decoding on the detection signals S included in the output data RD, thereby generating image data ID. More specifically, the signal processing circuit 45 includes a decoding circuit that performs an inverse operation on the detection signal S corresponding to an integrated value of the detection signals Si of a plurality of detection elements SE using the Hadamard matrix corresponding to the predetermined code, thereby decoding it into the detection signals Si of the respective detection elements SE. The detection signal Si corresponds to a signal of the intersection of the drive electrode Tx selected by the selection signal SELy and the detection electrode Rx selected by the selection signal SELx. The image data ID is two-dimensional information indicating the shape of an object to be detected (e.g., a finger) and a fingerprint.

The communication circuit 46 communicates with an external control circuit 100. The communication circuit 46 transmits the image data ID as output signals Vo to the external control circuit 100. The communication circuit 46 communicates with the external control circuit 100 by the serial peripheral interface (SPI), for example. The external control circuit 100 includes a communication circuit 146 and an authentication circuit 147, for example. The communication circuit 146 outputs the image data ID received from the communication circuit 46 to the authentication circuit 147. The authentication circuit 147 compares the image data ID with reference biological information on a user stored in advance. The authentication circuit 147 determines whether the image data ID matches the reference biological information, thereby performing authentication.

Alternatively, the detection circuit 40 does not necessarily include the signal processing circuit 45 and may output the output data RD stored in the memory 44 as output signals Vout. In this case, the external control circuit 100 includes a signal processing circuit 145. The signal processing circuit 145 receives the output data RD from the communication circuit 146 and generates the image data ID by performing the same signal processing as that performed by the signal processing circuit 45. The authentication circuit 147 performs authentication on the biological information based on the image data ID generated by the signal processing circuit 145. The detecting device 1 does not necessarily include the communication circuit 46 and may include the authentication circuit 147. In this case, the authentication circuit 147 performs authentication on the biological information based on the image data ID generated by the signal processing circuit 45 and outputs the results as the output signals Vout.

The detection circuit 40 and the detection control circuit 11 may be mounted on a peripheral region GA of a substrate 21 (refer to FIG. 2) as a detection integrated circuit (IC). Alternatively, the detection circuit 40 and the detection control circuit 11 may be included in a detection IC mounted on a wiring substrate 76 coupled to the peripheral region GA. Part of the functions of the detection circuit 40 may be provided as functions of an external micro-processing unit (MPU).

Figure 2:
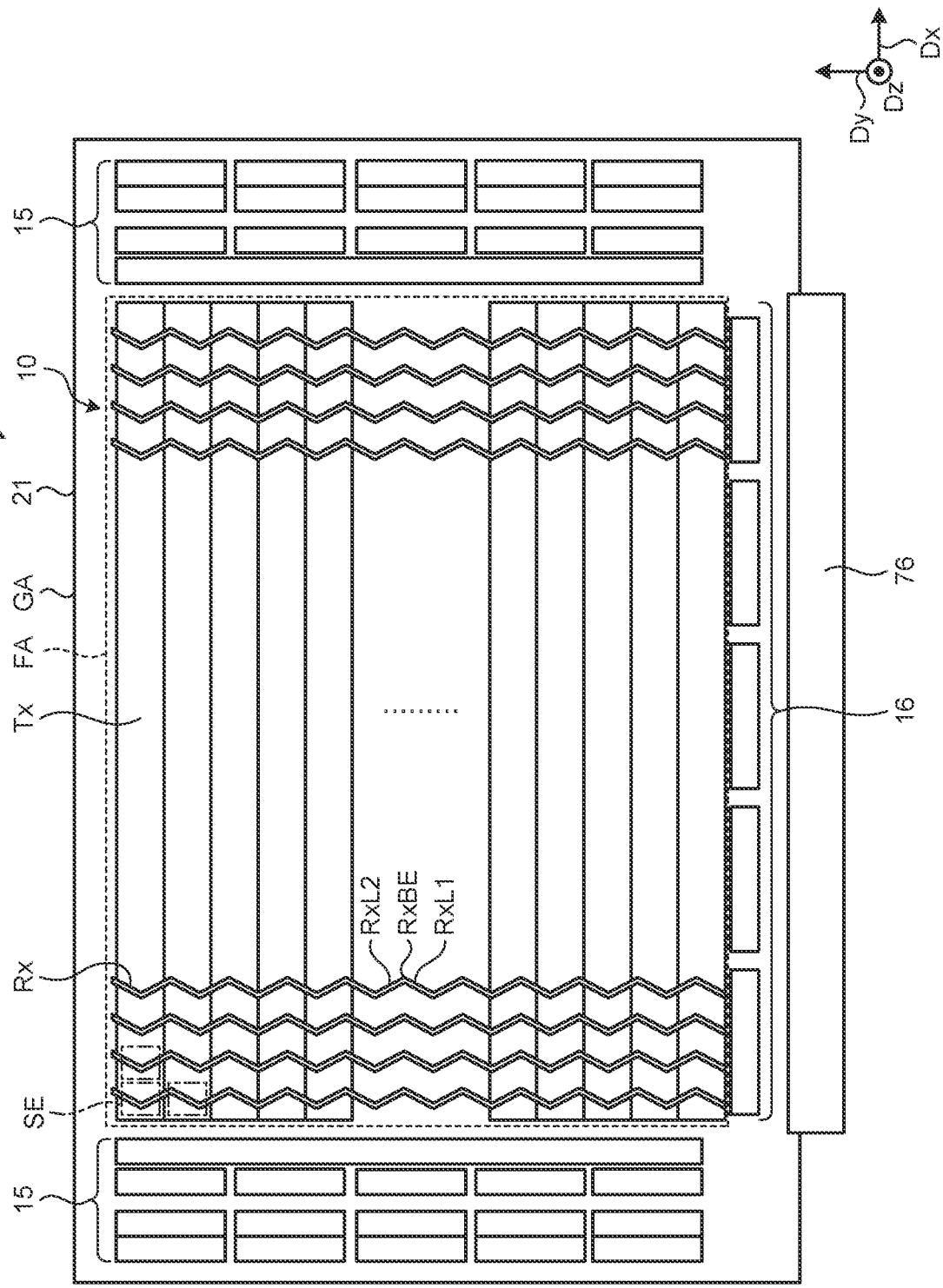
FIG. 2 is a plan view of an example of the configuration of the detecting device according to the embodiment.

The following describes the configuration of the detection electrodes Rx and the drive electrodes Tx of the detecting device 1. FIG. 2 is a plan view of an example of the configuration of the detecting device according to the embodiment.

As illustrated in FIG. 2, the detecting device 1 includes a substrate 21, a plurality of detection electrodes Rx, and a plurality of drive electrodes Tx. The substrate 21 is a translucent substrate that can allow visible light to pass therethrough and is a glass substrate, for example. The substrate 21 may be a translucent resin substrate or resin film made of resin, such as polyimide. The sensor 10 is a translucent sensor.

The drive electrodes Tx and the detection electrodes Rx are provided in the detection region FA. The drive electrodes Tx are disposed side by side in the second direction Dy. The drive electrodes Tx extend in the first direction Dx. The detection electrodes Rx are disposed side by side in the first direction Dx. The detection electrodes Rx extend in the second direction Dy. The drive electrodes Tx are provided intersecting the detection electrodes Rx in planar view. Intersections of the drive electrodes Tx and the detection electrodes Rx correspond to the respective sensor elements SE.

In the present specification, the first direction Dx and the second direction Dy are parallel to the surface of the substrate 21. The first direction Dx is orthogonal to the second direction Dy. The first direction Dx may intersect the second direction Dy without being orthogonal thereto. A third direction Dz is orthogonal to the first direction Dx and the second direction Dy. The third direction Dz corresponds to the normal direction of the substrate 21, for example. In the following description, planar view refers to the positional relation viewed from the third direction Dz.

The first selection circuit 15 and the second selection circuit 16 are provided in the peripheral region GA of the substrate 21. The drive electrodes Tx are electrically coupled to the first selection circuit 15. The detection electrodes Rx are electrically coupled to the wiring substrate 76 provided in the peripheral region GA of the substrate 21 via the second selection circuit 16. The wiring substrate 76 is flexible printed circuits, for example. Alternatively, the wiring substrate 76 may be a rigid substrate.

Capacitances are formed at the respective intersections of the detection electrodes Rx and the drive electrodes Tx. In the sensor 10, the first selection circuit 15 sequentially selects the drive electrodes Tx in a time-division manner and supplies the drive signals Vtx to the selected drive electrodes Tx. The detection electrodes Rx output the detection signals S corresponding to a change in capacitance between the drive electrodes Tx and the detection electrodes Rx due to the recesses and protrusions on the surface of a finger or the like in contact with or in proximity to the sensor 10. With this mechanism, the sensor 10 detects a fingerprint.

While various circuits, such as the first selection circuit 15 and the second selection circuit 16, are provided in the peripheral region GA of the substrate 21 in FIG. 2, this configuration is given by way of example only. At least part of the various circuits may be included in the detection IC mounted on the wiring substrate 76.

Figure 3:
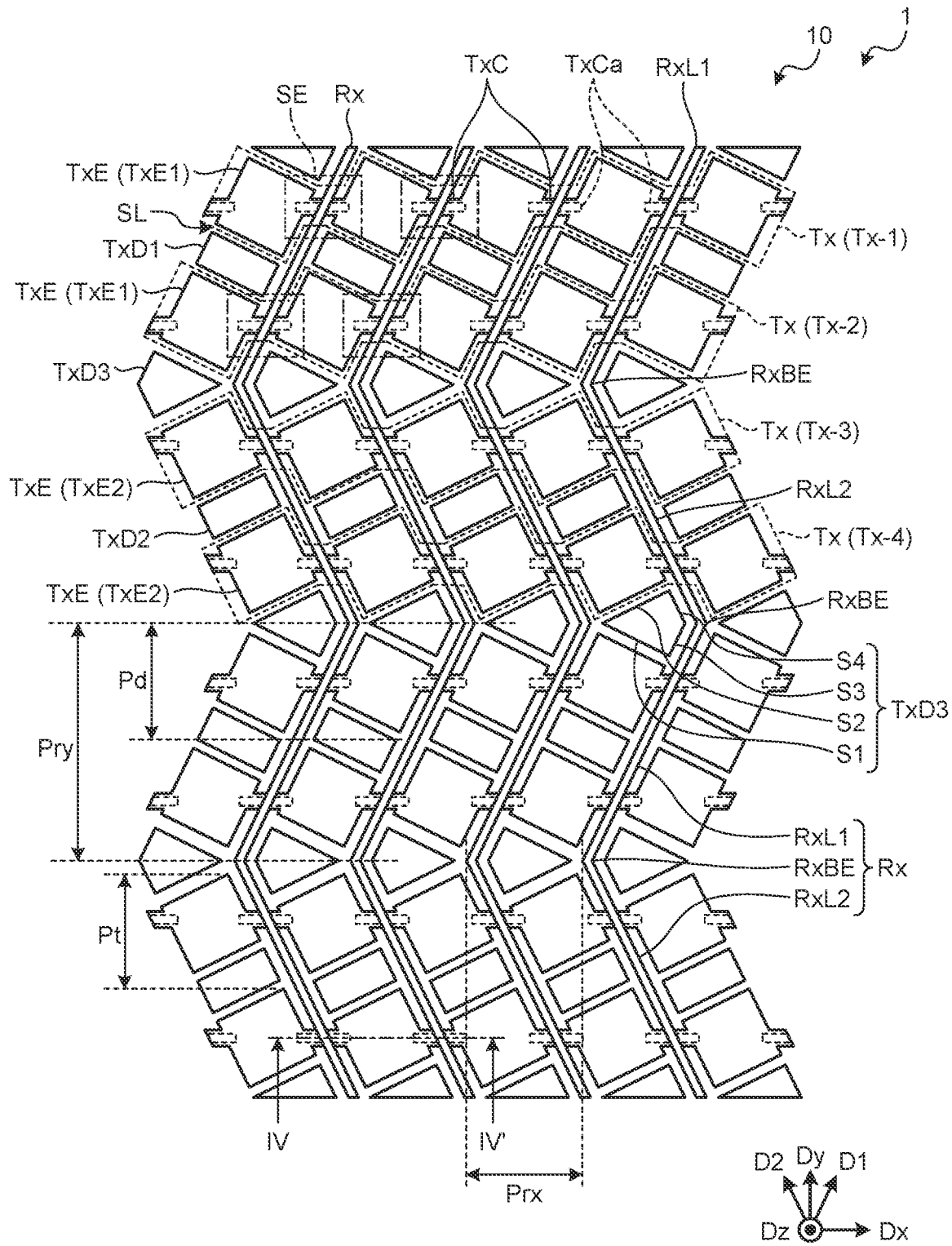
FIG. 3 is a plan view of drive electrodes and detection electrodes.

FIG. 3 is a plan view of the drive electrodes and the detection electrodes. As illustrated in FIG. 3, the detection electrode Rx is a zigzag metal thin wire in planar view. The detection electrode Rx extends in the second direction Dy as a whole. Specifically, the detection electrode Rx includes a plurality of first linear parts RxL1, a plurality of second linear parts RxL2, and a plurality of bent parts RxBE. The second linear parts RxL2 extend in a direction intersecting the first linear parts RxL1. The first linear parts RxL1 and the second linear parts RxL2 are metal thin wires. The bent part RxBE couples the first linear part RxL1 and the second linear part RxL2.

The first linear parts RxL1 extend in a D1 direction intersecting the first direction Dx and the second direction Dy. The second linear parts RxL2 extend in a D2 direction intersecting the first direction Dx and the second direction Dy. The D1 direction inclines opposite to the D2 direction with respect to the second direction Dy.

An arrangement interval Prx is an interval between the bent parts RxBE in the first direction Dx between the detection electrodes Rx disposed side by side. An arrangement interval Pry is an interval between the bent parts RxBE in the second direction Dy in each of the detection electrodes Rx. In the configuration according to the present embodiment, the arrangement interval Prx is smaller than the arrangement interval Pry, for example.

A plurality of drive electrodes Tx-1, Tx-2, Tx-3, Tx-4, . . . are disposed side by side in the second direction Dy. The drive electrodes Tx-1 and Tx-2 intersect the first linear parts RxL1 of the detection electrodes Rx. The drive electrodes Tx-3 and Tx-4 intersect the second linear parts RxL2 of the detection electrodes Rx. In the following description, the drive electrodes Tx-1, Tx-2, Tx-3, Tx-4, . . . are simply referred to as the drive electrodes Tx when they need not be distinguished from one another.

The drive electrodes Tx each include a plurality of electrode parts TxE and a plurality of coupling parts TxC. In each of the drive electrodes Tx, the electrode parts TxE are aligned in the first direction Dx and are separated from one another. In each of the drive electrodes Tx, the coupling part TxC couples the electrode parts TxE disposed side by side out of the electrode parts TxE. One detection electrode Rx extends between the electrode parts TxE disposed side by side and intersects the coupling part TxC when viewed from the third direction Dz. The electrode parts TxE and the coupling parts TxC are made of translucent conductive material, such as ITO.

The electrode parts TxE include first electrode parts TxE1 and second electrode parts TxE2 having a shape different from that of the first electrode parts TxE1. The first electrode part TxE1 and the second electrode part TxE2 have a parallelogrammatic shape when viewed from the third direction Dz. While the electrode parts TxE have a parallelogrammatic shape, they may have a rectangular, polygonal, or irregular shape.

The drive electrodes Tx-1 and Tx-2 each include a plurality of first electrode parts TxE1. The first electrode parts TxE1 are provided along the first linear part RxL1 and each have a square shape having two sides parallel to the first linear part RxL1 and two sides orthogonal to the first linear part RxL1. The drive electrodes Tx-3 and Tx-4 each include a plurality of second electrode parts TxE2. The second electrode parts TxE2 are provided along the second linear part RxL2 and each have a square shape having two sides parallel to the second linear part RxL2 and two sides orthogonal to the second linear part RxL2.

With this configuration, the first electrode parts TxE1 and the second electrode parts TxE2 are disposed along the zigzag detection electrode Rx. In addition, this configuration can make the distance between the detection electrode Rx and the electrode parts TxE constant. The number of electrode parts TxE corresponding to one first linear part RxL1 or one second linear part RxL2 may be one or an integer of 3 or larger.

Pt is an arrangement interval between the drive electrodes Tx in the second direction Dy. The arrangement interval Pt is substantially one-half of the arrangement interval Pry between the bent parts RxBE of the detection electrode Rx. The configuration is not limited thereto, and the arrangement interval Pt may be one-j-th (j is an integer of 1 or larger) of the arrangement interval Pry. The arrangement interval Pt is 50 μm to 100 μm, for example.

In one drive electrode Tx, the longitudinal direction of all the coupling parts TxC extends in the first direction Dx, and the coupling parts TxC are disposed on the same straight line. This configuration makes the shapes of the coupling parts TxC intersecting the detection electrodes Rx uniform, thereby suppressing variations in capacitance between the detection electrodes Rx and the coupling parts TxC. Metal layers TxCa are provided in regions overlapping the coupling parts TxC. This configuration can reduce the resistance of the multilayered body composed of the coupling part TxC and the metal layer TxCa if the width of the coupling part TxC is small.

The coupling parts TxC are not necessarily provided on the same straight line. The coupling parts TxC disposed side by side in the first direction Dx may be disposed at different positions in the second direction Dy. In this case, the metal layers TxCa having lower light transmittance than the electrode parts TxE are not aligned on one straight line. Consequently, the detecting device 1 can prevent unintended patterns, such as moire, from being generated.

Dummy electrodes TxD1, TxD2, and TxD3 are each provided between the drive electrodes Tx disposed side by side in the second direction Dy. Specifically, the dummy electrode TxD1 is provided between the first electrode parts TxE1 disposed side by side in the D1 direction, and the dummy electrode TxD2 is provided between the second electrode parts TxE2 disposed side by side in the D2 direction. The dummy electrode TxD3 is provided between the first electrode part TxE1 and the second electrode part TxE2. The dummy electrodes TxD1, TxD2, and TxD3 are separated from the electrode parts TxE by slits SL. In the following description, the dummy electrodes TxD1, TxD2, and TxD3 are simply referred to as dummy electrodes TxD when they need not be distinguished from one another. The dummy electrodes TxD are made of translucent conductive material, such as ITO, and are made of the same material as that of the drive electrodes Tx.

The dummy electrode TxD1 has a rectangular shape having two sides parallel to the first linear part RxL1 and two sides orthogonal to the first linear part RxL1. The dummy electrode TxD2 has a rectangular shape having two sides parallel to the second linear part RxL2 and two sides orthogonal to the second linear part RxL2. The dummy electrode TxD3 has a side s1 orthogonal to the first linear part RxL1, a side s2 orthogonal to the second linear part RxL2, a side s3 parallel to the first linear part RxL1, and a side s4 parallel to the second linear part RxL2. An arrangement interval Pd between the dummy electrodes TxD in the second direction Dy is equal to the arrangement interval Pt between the drive electrodes Tx.

The slits SL formed with the detection electrode Rx interposed therebetween are not aligned on the same straight line. In other words, the electrode part TxE is disposed across the detection electrode Rx from the slit SL in the extending direction of the slit SL. With this configuration, the part not provided with the electrode parts TxE or the dummy electrodes TxD is formed to bend at a small pitch. Consequently, the detecting device 1 can prevent unintended patterns (e.g., moire and patterns due to reflection of light) from being generated in the detection region FA.

In the sensor 10 illustrated in FIG. 3, the positional relation between the shape of the drive electrodes Tx and the shape of the detection electrodes Rx is uniform between the electrodes. This configuration has small variations in capacitance of the drive electrodes Tx and in capacitance of the detection electrodes Rx. In addition, this configuration facilitates correction in calculating the coordinates in the sensor 10, for example.

Figure 4:
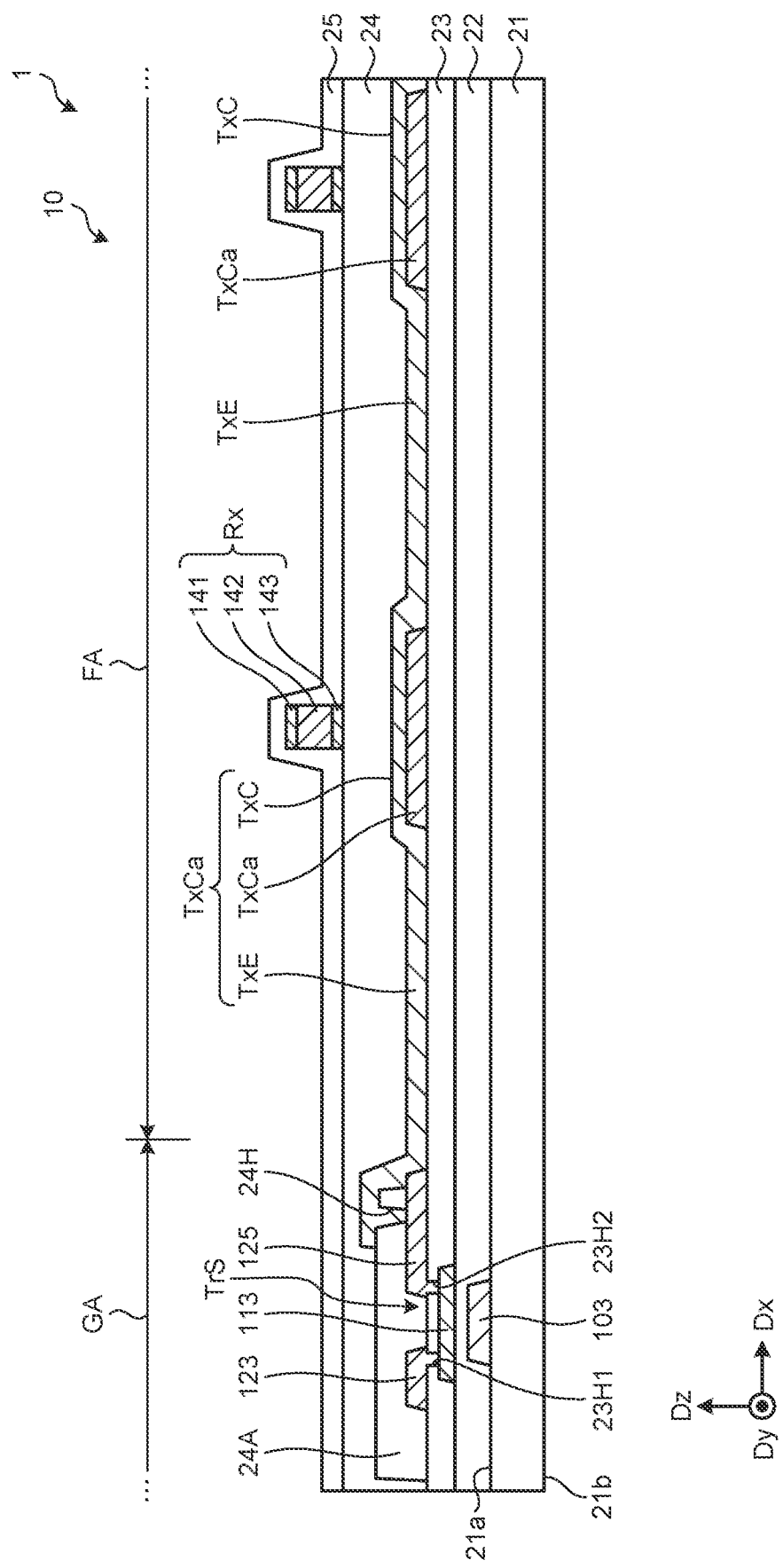
FIG. 4 is a sectional view along line IV-IV' of FIG. 3.

FIG. 4 is a sectional view along line IV-IV' of FIG. 3. To illustrate the relation between the layer structure of the detection region FA and the layer structure of the peripheral region GA, FIG. 4 schematically connects the section along line IV-IV' of the detection region FA and the section of the part including a transistor TrS of the peripheral region GA. The transistor TrS is an element included in the first selection circuit 15.

As illustrated in FIG. 4, the substrate 21 has a first surface 21a and a second surface 21b opposite to the first surface 21a. The drive electrode Tx and the detection electrodes Rx are provided on the first surface 21a of the substrate 21. Specifically, an insulating film 22 and an insulating film 23 are layered on the first surface 21a. The drive electrode Tx is provided on the insulating film 23. The electrode parts TxE and the metal layers TxCa are provided on the insulating film 23, and the coupling parts TxC are provided covering the respective metal layers TxCa. An insulating film 24 is provided on the insulating film 23 and covers the drive electrode Tx.

The detection electrodes Rx are provided on the insulating film 24 in the detection region FA. The detection electrodes Rx are each provided at a position overlapping the coupling part TxC and the metal layer TxCa. The insulating film 24 provides insulation between the detection electrodes Rx and the drive electrode Tx. The detection electrode Rx includes a first metal layer 141, a second metal layer 142, and a third metal layer 143, for example. The second metal layer 142 is provided on the third metal layer 143, and the first metal layer 141 is provided on the second metal layer 142.

The first metal layer 141 and the third metal layer 143 are made of molybdenum (Mo) or a molybdenum alloy, for example. The second metal layer 142 is made of aluminum (Al) or an aluminum alloy. The first metal layer 141 has lower reflectance of visible light than the second metal layer 142.

An insulating film 25 is provided on the detection electrodes Rx and the insulating film 24. The insulating film 25 covers the upper surfaces and the side surfaces of the detection electrodes Rx. The insulating film 25 is a film having a high refractive index and low reflectance, such as a silicon nitride film, a silicon oxynitride film, and acrylic resin.

The drive electrode Tx extends from the detection region FA to the peripheral region GA and is coupled to the transistor TrS. The transistor TrS includes a gate electrode 103, a semiconductor layer 113, a source electrode 123, and a drain electrode 125. The gate electrode 103 is provided on the substrate 21. The insulating film 22 is provided on the gate electrode 103. The semiconductor layer 113 is provided on the insulating film 22. The gate electrode 103 may be provided on the semiconductor layer 113.

The insulating film 23 is provided on the semiconductor layer 113. The source electrode 123 and the drain electrode 125 are provided on the insulating film 23. The source electrode 123 is coupled to the semiconductor layer 113 through a contact hole 23H1 formed in the insulating film 23. The drain electrode 125 is coupled to the semiconductor layer 113 through a contact hole 23H2 formed in the insulating film 23.

An insulating film 24A is provided on the source electrode 123 and the drain electrode 125. The drive electrode Tx is coupled to the drain electrode 125 through a contact hole 24H formed in the insulating film 24A. While the insulating film 24 and the insulating film 24A are provided in different layers, the configuration is not limited thereto. The insulating film 24, for example, is disposed on the transistor TrS and the metal layer TxCa, and the insulating film 24 on the metal layer TxCa is disposed so as to provide insulation between the third metal layer 143 and the metal layer TxCa. In this case, the coupling part TxC covers part of the metal layer TxCa around the insulating film 24 on the metal layer TxCA in a manner not electrically coupled to the third metal layer 143. The insulating film 25 covers the electrode parts TxE and other components not covered with the insulating film 24.

Figure 5:
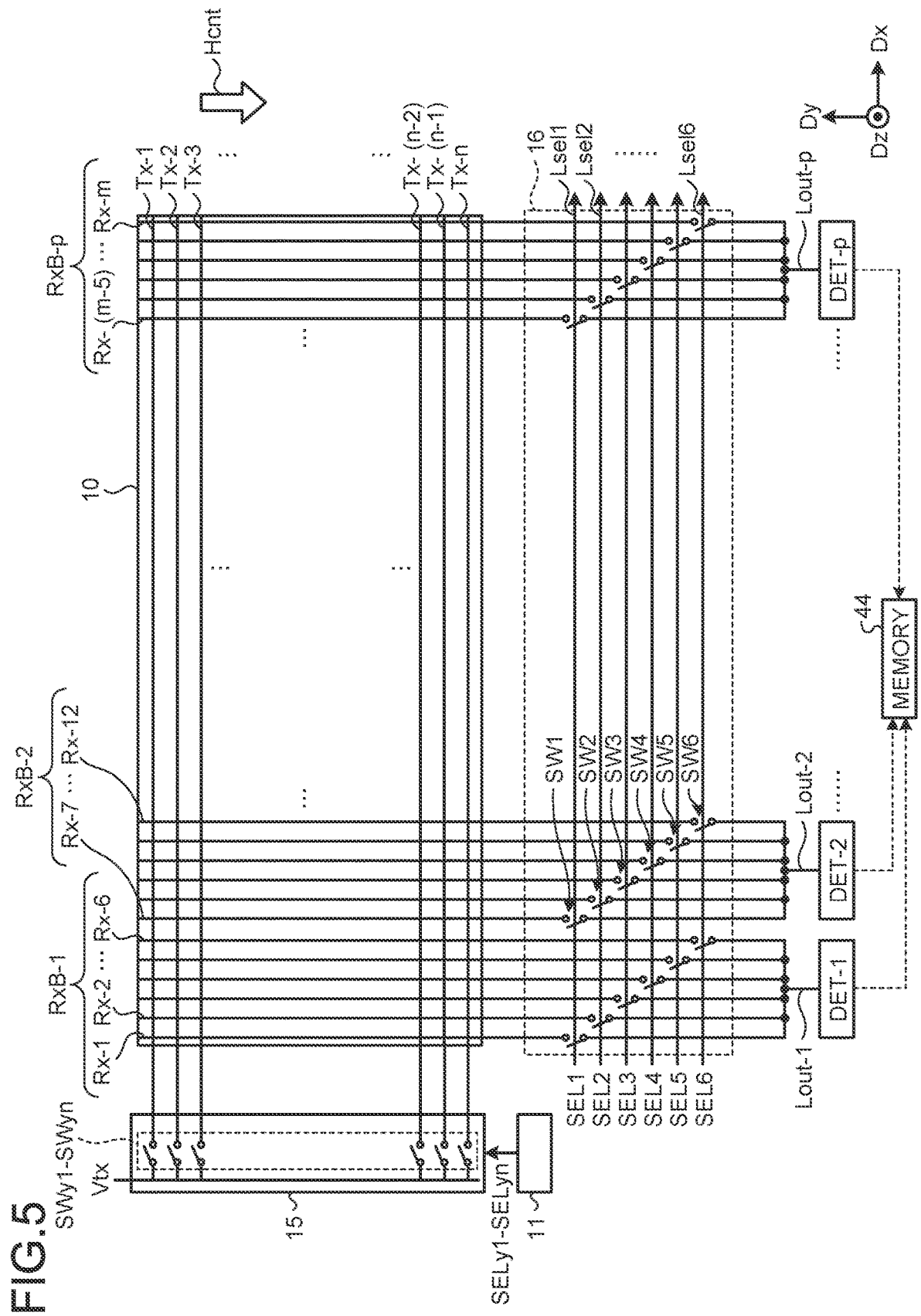
FIG. 5 is a diagram for explaining a sensor, a second selection circuit, detectors, and a memory according to the embodiment.

The following describes the method for driving the detecting device 1. FIG. 5 is a diagram for explaining the sensor, the second selection circuit, the detectors, and the memory according to the embodiment. FIG. 5 schematically illustrates the drive electrodes Tx and the detection electrodes Rx as straight lines.

As illustrated in FIG. 5, m detection electrodes Rx-1, Rx-2, . . . , and Rx-m are arrayed in the first direction Dx. The number m of detection electrodes Rx is 192, for example. n drive electrodes Tx-1, Tx-2, . . . , and Tx-n are arrayed in the second direction Dy. The number n of drive electrodes Tx is 256, for example. In other words, m×n sensor elements SE are disposed.

A plurality of detection electrode blocks RxB are provided. One detection electrode block RxB is composed of a plurality of detection electrodes Rx disposed side by side. In the example illustrated in FIG. 5, the number k of detection electrodes Rx included in one detection electrode block RxB is 6. A detection electrode block RxB-1 includes the detection electrodes Rx-1, Rx-2, . . . , and Rx-6. A detection electrode block RxB-2 includes the detection electrodes Rx-7, . . . , and Rx-12. A detection electrode block RxB-p includes the detection electrodes Rx-(m−5), . . . , and Rx-m. The number p of detection electrode blocks RxB is one-k-th of the number m of detection electrodes Rx (p=m/6 is satisfied in FIG. 5).

A plurality of detectors DET-1, DET-2, . . . , and DET-p are provided corresponding to the detection electrode blocks RxB-1, RxB-2, . . . , and RxB-p, respectively. More specifically, the detectors DET-1, DET-2, . . . , and DET-p are coupled to the detection electrode blocks RxB-1, RxB-2, . . . , and RxB-p via the second selection circuit 16 and a plurality of output signal lines Lout-1, Lout-2, . . . , and Lout-p, respectively.

The detector DET is coupled to the detection electrode Rx selected by the second selection circuit 16 out of the detection electrodes Rx. In the detection electrode block RxB-1, one or a plurality of detection electrodes Rx selected by the second selection circuit 16 are coupled to the detector DET-1 via the output signal line Lout-1. In the detection electrode block RxB-p, one or a plurality of detection electrodes Rx selected by the second selection circuit 16 are coupled to the detector DET-p via the output signal line Lout-p.

The second selection circuit 16 includes a plurality of selection signal lines Lsel-1, Lsel-2, . . . , and Lsel-6 and a plurality of switching elements SWx1, SWx2, . . . , and SWx6. The switching elements SWx1, SWx2, . . . , and SWx6 are provided to each of the detection electrode blocks RxB. The switching elements SWx1, SWx2, . . . , and SWx6 are supplied with selection signals SELx1, SELx2, . . . , and SELx6 via the selection signal lines Lsel-1, Lsel-2, . . . , and Lsel-6, respectively. The switching elements SWx1, SWx2, . . . , and SWx6 switches coupling and decoupling between the detection electrode Rx and the output signal line Lout based on the selection signals SELx1, SELx2, . . . , and SELx6, respectively.

When a plurality of switching elements SWx1 are supplied with the selection signals SELx1 at a high-level voltage, for example, the switching elements SWx1 are turned on. Consequently, the detection electrodes Rx-1, Rx-7, . . . , and Rx-(m−5) selected in the detection electrode blocks RxB are in a state coupled to the output signal lines Lout-1, Lout-2, . . . , and Lout-p and are coupled to the detectors DET-1, DET-2, . . . , and DET-p, respectively. As a result, the selected detection electrodes Rx output the detection signals S to the respective detectors DET.

By contrast, when a plurality of switching elements SWx2, . . . , and SWx6 are supplied with the selection signals SELx2, . . . , and SELx6 at a low-level voltage, respectively, the switching elements SWx2, . . . , and SWx6 are turned off. Consequently, the detection electrodes Rx not selected in the detection electrode blocks RxB are in a state not coupled to the output signal lines Lout. As a result, the non-selected detection electrodes Rx do not output the detection signals S to the respective detectors DET. The detection control circuit 11 supplies the selection signals SELx1 to SELx6 at a high-level voltage in a time-division manner, thereby sequentially selecting the detection electrodes Rx in the detection electrode blocks RxB.

The first selection circuit 15 includes a plurality of switching elements SWy1, SWy2, SWy3, . . . , SWyn−2, SWyn−1, and SWyn. First ends of the switching elements SWy are coupled to the respective n drive electrodes Tx, and second ends thereof are coupled to wiring L1 for supplying the drive signals Vtx. The switching elements SWy couple the selected drive electrodes Tx to the wiring L1 based on selection signals SELy1 to SELy256 supplied from the detection control circuit 11, thereby supplying the drive signals Vtx to the selected drive electrodes Tx.

Figure 6:
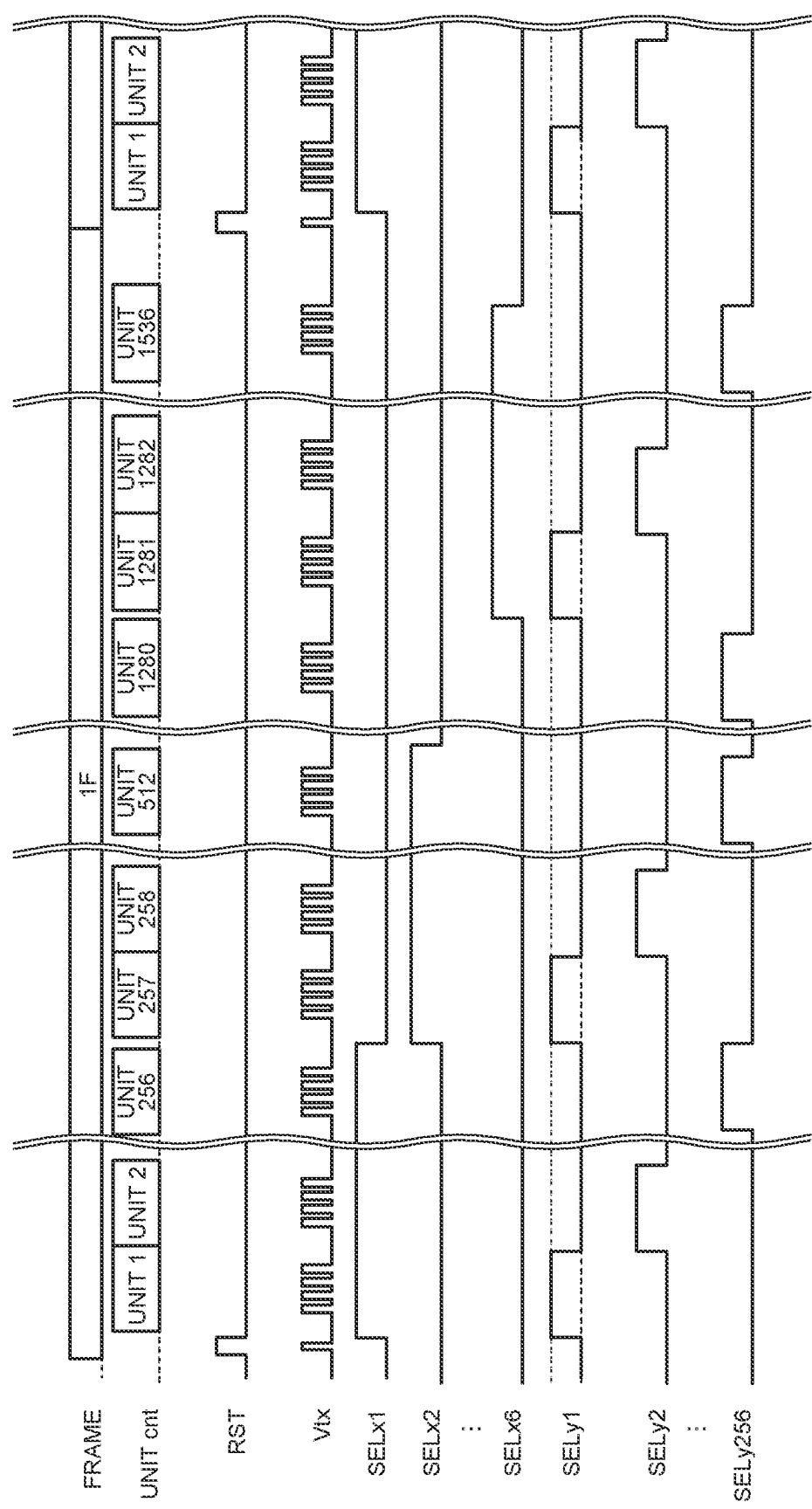
FIG. 6 is a timing chart of an operation performed by the detecting device according to the embodiment.

FIG. 6 is a timing chart of an operation performed by the detecting device according to the embodiment. FIG. 6 is a timing chart of a period for performing detection of one frame (1 F). Detection of one frame is detection on the whole detection region FA and indicates a period required to detect the detection signals S at all the intersections of the drive electrodes TX and the detection electrodes Rx.

As illustrated in FIG. 6, detection of one frame is started based on a reset signal RST supplied from the detection control circuit 11. The counter circuit 11a sequentially counts a unit count (unit cnt). The unit count increments by 1 for each combination pattern of the selected drive electrode Tx and the selected detection electrode Rx. When the number k of detection electrodes Rx included in the detection electrode block RxB is 6, and the number n of drive electrodes Tx is 256, for example, detection of one frame is finished when the unit count is counted to 6×256=1536.

When detection of one frame is started, the detection control circuit 11 sequentially supplies the selection signals SELx1, SELx2, . . . , and SELx6 in a time-division manner to the second selection circuit 16. The second selection circuit 16 selects one or a plurality of detection electrodes Rx in a time-division manner out of the detection electrodes Rx included in each of the detection electrode blocks RxB based on the selection signals SELx1, SELx2, . . . , and SELx6.

In a period when the selection signal SELx at a high-level voltage is supplied to the second selection circuit 16, the selection signals SELy are supplied to the first selection circuit 15 in a time-division manner. In one period when the second selection circuit 16 simultaneously selects a plurality of detection electrodes Rx (e.g., the detection electrodes Rx-1, Rx-7, . . . , and Rx-(m−5)), for example, the first selection circuit 15 sequentially scans the drive electrodes Tx. In other words, in a period when the sensor elements SE (detection electrodes Rx) of certain columns are selected by the selection signal SELx, an operation for selecting the sensor elements (drive electrode Tx) of a certain row is performed in all the selection patterns based on the selection signals SELy1, . . . , and SELyn corresponding to a predetermined code.

The selection signal SELy corresponds to a gate drive signal for the transistor TrS (refer to FIG. 4) included in the first selection circuit 15. When the selection signal SELy is at a high-level voltage, the transistor TrS is turned on, and the corresponding drive electrode Tx is selected. The selected drive electrode Tx is supplied with the drive signals Vtx.

Specifically, the second selection circuit 16 is supplied with the selection signal SELx1 (first selection signal) at a high-level voltage. Based on the selection signal SELx1, the second selection circuit 16 simultaneously selects the detection electrodes Rx-1, Rx-7, . . . , and Rx-(m−5) (first detection electrodes) from the respective detection electrode blocks RxB. In a period when the selection signal SELx1 is turned on (high-level voltage), the first selection circuit 15 is supplied with the selection signals SELy1, SELy2, . . . , and SELy256 in a time-division manner. As a result, the first selection circuit 15 sequentially scans the drive electrodes Tx. The period when each of the selection signals SELy1, SELy2, . . . , and SELy256 is turned on is shorter than the period when the selection signal SELx1 is turned on.

After the drive electrodes Tx corresponding to all the selection patterns are scanned based on all the selection signals SELy1 to SELy256, the second selection circuit 16 is supplied with the selection signal SELx2 (second selection signal) at a high-level voltage. Based on the selection signal SELx2, the second selection circuit 16 simultaneously selects the detection electrodes Rx-2, Rx-8, . . . , and Rx-(m−4) (second detection electrodes) from the respective detection electrode blocks RxB. In a period when the selection signal SELx2 is turned on (high-level voltage), the first selection circuit 15 is supplied with the selection signals SELy1, SELy2, . . . , and SELy256 in a time-division manner. As a result, the first selection circuit 15 sequentially scans the drive electrodes Tx based on the selection patterns indicated by the respective selection signals SELy. This drive is repeatedly performed from the selection signal SELx3 to the selection signal SELx6, and detection of one frame is finished.

Figure 7:
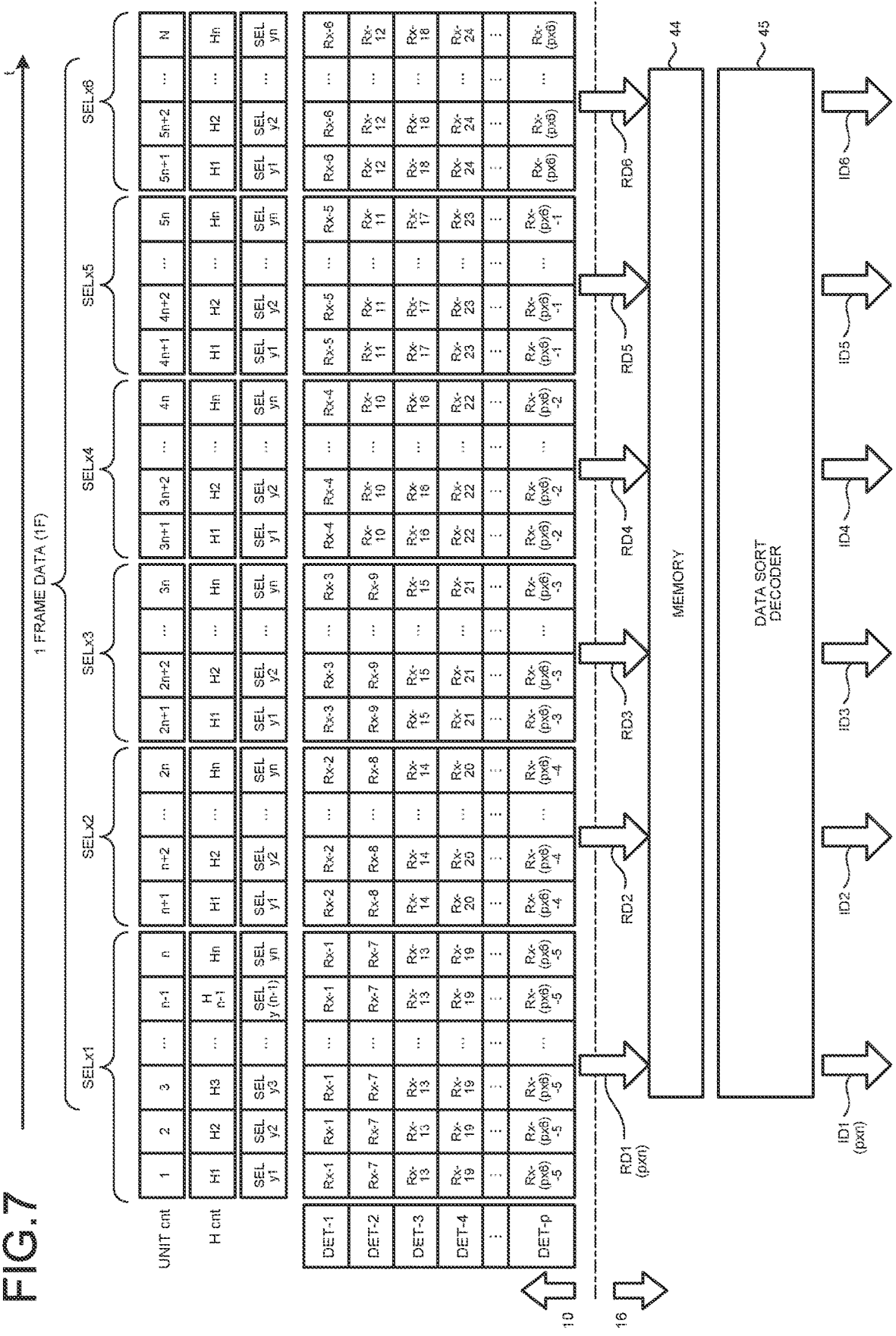
FIG. 7 is a diagram for explaining the relation between selected drive electrodes and selected detection electrodes in one frame period.

FIG. 7 is a diagram for explaining the relation between the selected drive electrodes and the selected detection electrodes in one frame period. In FIG. 7, time t elapses from the left side to the right side.

As illustrated in FIG. 7, in a period when the selection signal SELx1 is turned on, the second selection circuit 16 selects the detection electrodes Rx-1, Rx-7, Rx-13, Rx-19, . . . , and Rx-((px6)−5). The selected detection electrodes Rx are coupled to the respective detectors DET. The first selection circuit 15 scans the drive electrodes Tx corresponding to the selection patterns indicated by the selection signals SELy1, . . . , and SELyn while maintaining the selection pattern of the selected detection electrodes Rx. An H count (Hcnt) illustrated in FIG. 7 increments by 1 every time the first selection circuit 15 scans the drive electrode Tx once based on the selection pattern indicated by the selection signal SELy. When the first selection circuit 15 finishes scanning the drive electrode Tx corresponding to the selection pattern indicated by the selection signal SELyn, the H count is reset. In other words, when the H count is counted to Hn, turning-on and -off the selection signal SELx is switched.

When the selection signal SELx1 is turned on, and the H count is H1, the drive signals Vtx are supplied to the drive electrode Tx corresponding to the selection pattern indicated by the selection signal SELy1, and a plurality of (p) selected detection electrodes Rx output the detection signals S to the respective detectors DET. In one period when the drive electrode Tx corresponding to the selection pattern indicated by the selection signal SELy1 is selected, p detection signals S are output. In the period when the selection signal SELx1 is turned on, the H count is counted from H1 to Hn. In other words, in each of n periods when the drive electrodes Tx are scanned based on the selection patterns indicated by the selection signals SELy1, . . . , and SELyn, the selected detection electrodes Rx sequentially output p detection signals S. As a result, the memory 44 stores therein pxn detection signals S output from the selected detection electrodes Rx via the detectors DET in a period when the selection signal SELx1 is turned on as a set of output data RD1.

In other words, the set of output data RD1 is digital data output from the detectors DET and received by the memory 44 in a period when the selection signal SELx1 is turned on and is digital data constituting part of the output data RD of one frame. More specifically, the set of output data RD1 is composed of the detection signals S output from the p detection electrodes Rx selected by the second selection circuit 16 when all the drive electrodes Tx are scanned and does not include information on the detection signals S output from the non-selected detection electrodes Rx.

Similarly, the drive electrodes Tx are scanned based on the selection patterns indicated by the selection signals SELy1, . . . , and SELyn in each of the periods when the selection signals SELx2, SELx3, . . . , and SELx6 are supplied to the second selection circuit 16. The memory 44 stores therein sets of output data RD2, RD3, RD4, RD5, and RD6 in the respective periods. In other words, the memory 44 stores therein the detection signals S output based on each of the different selection signals SELx1, SELx2, . . . , and SELx6 as the different output data RD1, RD2, . . . , and RD6.

The signal processing circuit 45 receives the output data RD1, RD2, . . . , and RD6 and performs signal processing, such as sorting and decoding. As a result, the signal processing circuit 45 generates image data ID1, ID2, . . . , and ID6 based on the output data RD1, RD2, . . . , and RD6, respectively.

The signal processing circuit 45 outputs the image data ID1, ID2, . . . , and ID6 to an external circuit via the communication circuit 46. The external circuit integrates the image data ID1, ID2, . . . , and ID6 to obtain biological information, such as a fingerprint of the user. The signal processing circuit 45 may generate one image datum ID based on the output data RD1, RD2, . . . , and RD6.

FIG. 8 is a diagram for explaining a selection operation performed by the first selection circuit. The first selection circuit 15 performs a code selection operation for selecting the sensor elements SE (drive electrodes Tx) based on a predetermined code. To facilitate the reader's understanding, FIG. 8 illustrates an example where the first selection circuit 15 performs the code selection operation on four sensor elements SE (drive electrodes Tx) based on a Hadamard matrix the order of which is 4 in Expression (1) as the predetermined code. The order of the Hadamard matrix corresponding to the predetermined code is not limited to 4. The order may be a value of 4 or larger, and the number of sensor elements SE (drive electrodes Tx) arrayed in the second direction Dy corresponding to the predetermined code may be 4 or more. FIG. 8A illustrates a period Tc1 when the selection signal SELy1 is supplied to the first selection circuit, FIG. 8B illustrates a period Tc2 when the selection signal SELy2 is supplied to the first selection circuit, FIG. 8C illustrates a period Tc3 when the selection signal SELy3 is supplied to the first selection circuit, and FIG. 8D illustrates a period Tc4 when the selection signal SELy4 is supplied to the first selection circuit. The selection signals SELy1, SELy2, SELy3, and SELy4 include selection signals SELyp (SELy1$p$, SELy2$p$, SELy3$p$, and SELy4$p$) for selecting the sensor elements SE (drive electrodes Tx) corresponding to "1" in the columns of the Hadamard matrix and selection signals SELym (SELy1$m$, SELy2$m$, SELy3$m$, and SELy4$m$) for selecting the sensor elements SE (drive electrodes Tx) corresponding to "−1" of the Hadamard matrix, respectively. The periods Tc1, Tc2, Tc3, and Tc4 include periods Tcp (Tc1$p$, Tc2$p$, Tc3$p$, and Tc4$p$) in which selection is performed by the selection signals SELyp and periods Tcm (Tc1$m$, Tc2$m$, Tc3$m$, and Tc4$m$) in which selection is performed by the selection signals SELym, respectively.

$$H_v = \begin{pmatrix} 1 & 1 & 1 & 1 \\ 1 & 1 & -1 & -1 \\ 1 & -1 & -1 & 1 \\ 1 & -1 & 1 & -1 \end{pmatrix} \quad (1)$$

Figure 8A:
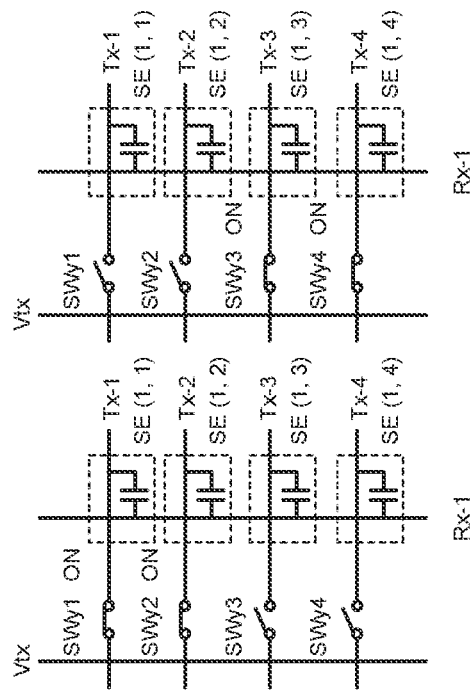
FIG. 8A is a diagram for explaining a selection operation performed by a first selection circuit.
Figure 8B:
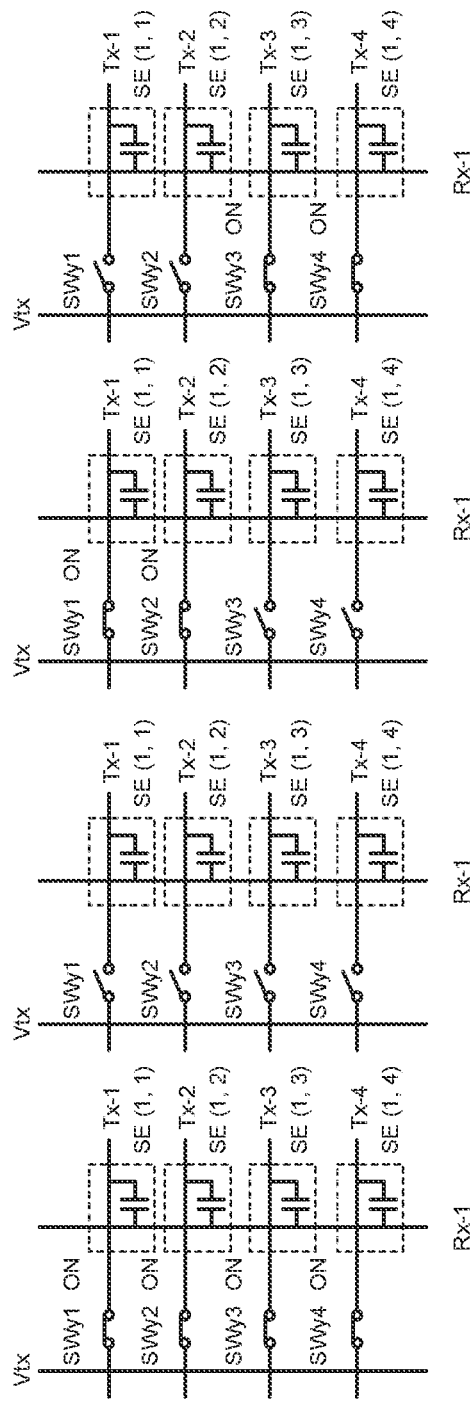
FIG. 8B is a diagram for explaining a selection operation performed by a first selection circuit.
Figure 8C:
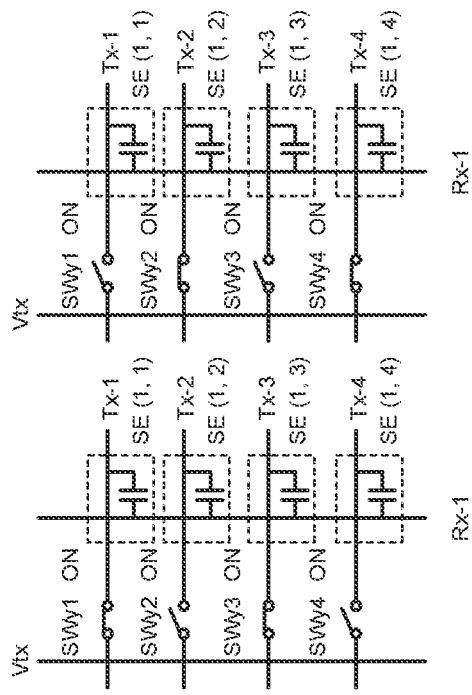
FIG. 8C is a diagram for explaining a selection operation performed by a first selection circuit.
Figure 8D:
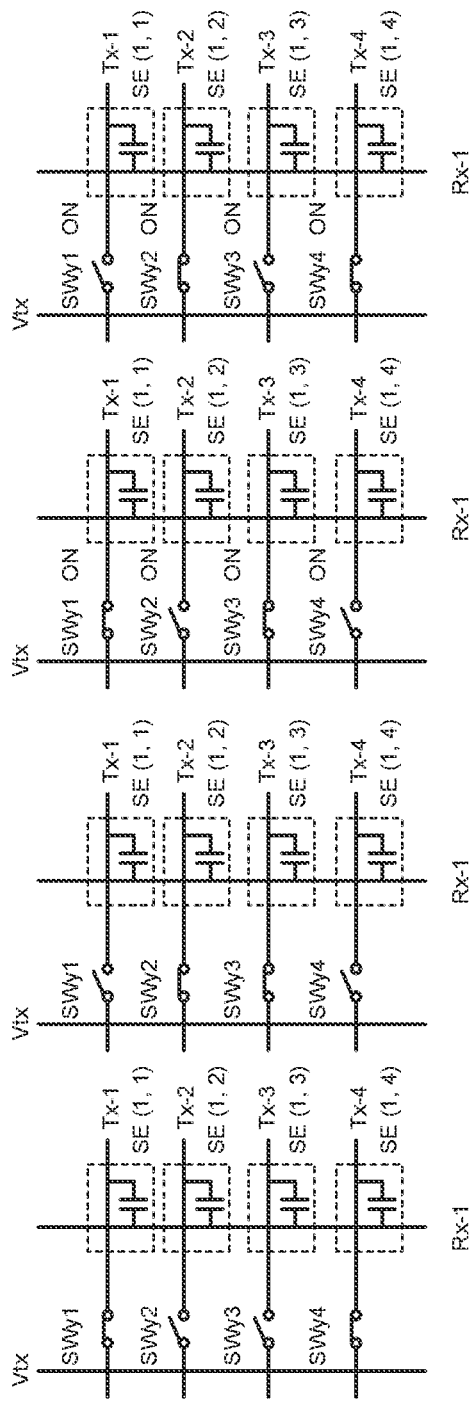
FIG. 8D is a diagram for explaining a selection operation performed by a first selection circuit.

In the period Tc1$p$, the detection control circuit 11 supplies the selection signal SELy1$p$ as illustrated in FIG. 8A. The selection signal SELy1$p$ corresponds to "1" in the first column of the Hadamard matrix, and all the drive electrodes Tx1, Tx2, Tx3, and Tx4 are coupled to the wiring L1 and are supplied with the drive signals Vtx. The detection electrodes Rx output detection signals S1$p$. In the period Tc1$m$, the detection control circuit 11 supplies the selection signal SELy1$m$. The selection signal SELy1$m$ corresponds to "−1" in the first column of the Hadamard matrix, and none of the drive electrodes Tx1, Tx2, Tx3, and Tx4 is coupled to the wiring L1 and is supplied with the drive signals Vtx. The detection electrodes Rx output detection signals S1$m$. Similarly, detection signals S2$p$, S2$m$, S3$p$, S3$m$, S4$p$, and S4$m$ corresponding to the selection signals SELyp and SELym are sequentially output as illustrated in FIGS. 8B, 8C, and 8D.

A signal processor obtains the detection signal S by subtracting the detection signal Sm from the detection signal Sp. The signal processor decodes the detection signal S by performing an inverse operation using the Hadamard matrix and obtains the detection signals from the respective sensor elements SE. The detection signal S is not necessarily obtained by subtracting the detection signal Sm from the detection signal Sp. The detection signal S may be calculated by deriving only one of the detection signal Sp and the detection signal Sm and performing an inverse operation using the Hadamard matrix by a predetermined arithmetic expression. As a result, one of the periods Tcp and Tcm for selecting the sensor elements SE based on the selection signal SELyp or SELym can be omitted.

Figure 9:
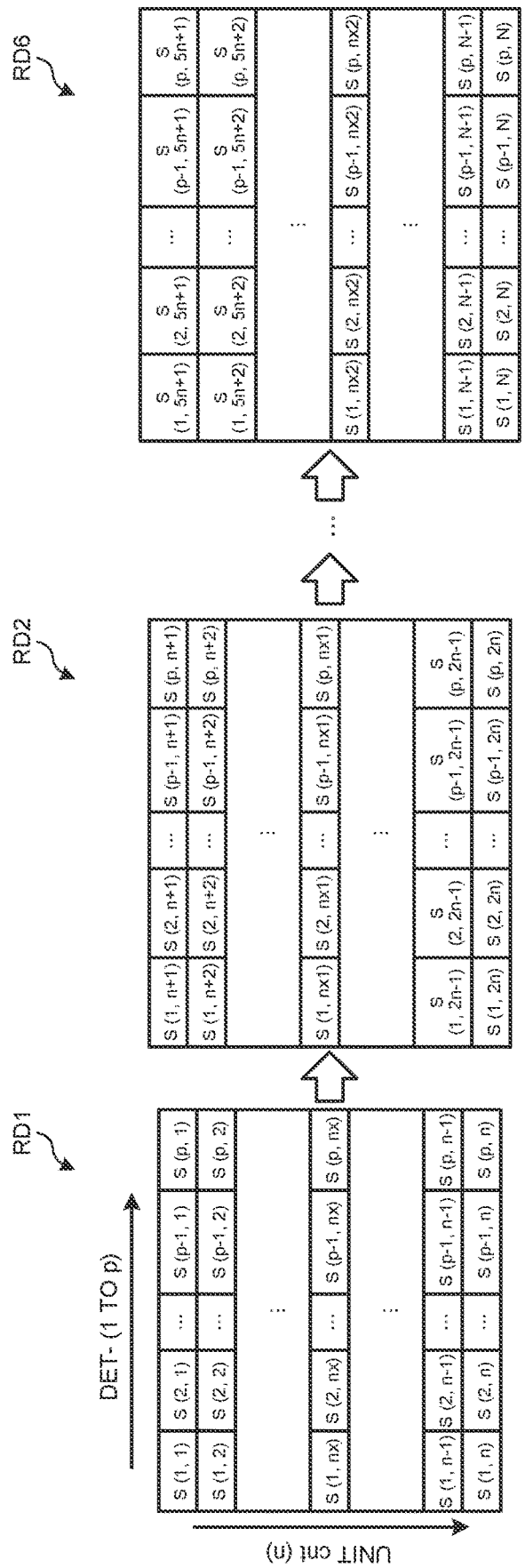
FIG. 9 is a diagram for explaining an example of output data stored in the memory.

FIG. 9 is a diagram for explaining an example of the output data stored in the memory. In the output data RD, the detection signals S output from the detectors DET (DET-1 to DET-p) are stored in parallel for each unit count (or each H count). The detection signals S are stored in a manner associated with the numbers of the detectors DET (1 to p) and the count number n of the unit count (or the H count).

In the output data RD1, for example, detection signals S(1,1) to S(p,n) are stored as a set of data. In the output data RD2, detection signals S(1,n+1) to S(p,2n) are stored as a set of data. Similarly, in the output data RD6, detection signals S(1,5n+1) to S(p,N) are stored as a set of data where N is 6×n.

Figure 10:
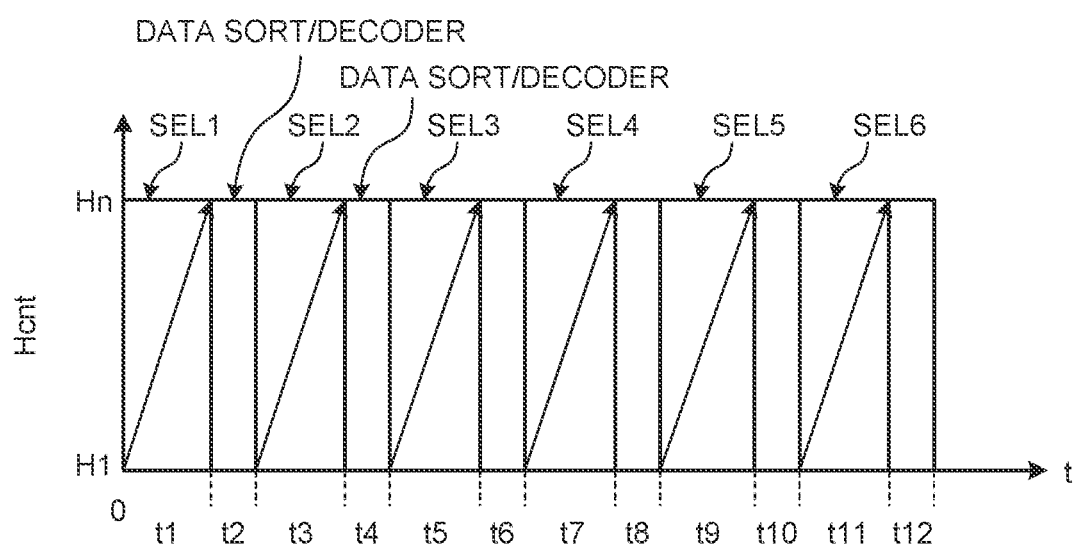
FIG. 10 is a diagram for explaining the relation between output data acquisition periods and signal processing periods.

FIG. 10 is a diagram for explaining the relation between output data acquisition periods and signal processing periods. In FIG. 10, the horizontal axis indicates time, and the vertical axis indicates the count number of the H count. As illustrated in FIG. 10, the detecting device 1 repeatedly performs storing therein the output data RD and generating the image data ID in each period included in detection of one frame. Specifically, in a period t1, the second selection circuit 16 selects the detection electrodes Rx based on the selection signal SELx1, and the first selection circuit 15 scans the drive electrodes Tx based on the selection signals SELy1, . . . , and SELyn. As a result, the memory 44 acquires the output data RD1.

In a period t2 subsequent to the period t1, the signal processing circuit 45 receives the output data RD1 from the memory 44 and performs signal processing, such as sorting and decoding. As a result, the signal processing circuit 45 generates the image data ID1 based on the output data RD1.

In a period t3 subsequent to the period t2, the second selection circuit 16 selects the detection electrodes Rx based on the selection signal SELx2, and the first selection circuit 15 scans the drive electrodes Tx based on the selection signals SELy1, . . . , and SELyn. As a result, the memory 44 acquires the output data RD2.

In a period t4 subsequent to the period t3, the signal processing circuit 45 receives the output data RD2 from the memory 44 and outputs the image data ID2 based on the output data RD2.

As described above, the detecting device 1 stores therein a plurality of different output data RD1, RD2, . . . , and RD6 in a time-division manner in a period for performing detection of one frame. The periods t1, t3, t5, t7, t9, and t11 in which the memory 44 stores therein the output data RD1, RD2, . . . , and RD6 and the periods t2, t4, t6, t8, t10, and t12 in which the signal processing circuit 45 performs signal processing are alternately arranged.

There is a comparative example of the method for driving the detecting device 1. In this comparative example, the second selection circuit 16 sequentially scans the detection electrodes Rx based on the selection signals SELx1 to SELx6 in a period when the first selection circuit 15 selects the drive electrode Tx based on one selection signal SELy1, for example. Every time the first selection circuit 15 changes the selection pattern of the drive electrode Tx based on the selection signals SELy2, . . . , and SELyn, the second selection circuit 16 selects the detection electrodes Rx based on the selection signals SELx1 to SELx6. To perform signal processing, the signal processing circuit 45 requires the detection signals S obtained by scanning the drive electrodes Tx based on all the selection patterns corresponding to the selection signals SELy1, . . . , and SELyn. The memory 44 stores therein the detection signals S of one frame, that is, m×n detection signals S as a set of output data.

In the detecting device 1 according to the present embodiment, the first selection circuit 15 scans a plurality of drive electrodes Tx in one period when the second selection circuit 16 selects a plurality of detection electrodes Rx as described above. In other words, the drive electrodes Tx are scanned based on all the selection patterns corresponding to the selection signals SELy1, . . . , and SELyn in a period when one selection signal SELx is at a high-level voltage. As a result, the memory 44 stores therein a plurality of detection signals S output from the selected detection electrodes Rx via the detectors DET as a set of output data RD. The number of detection signals S included in the output data RD is reduced to p×n, which is the product of the number of detectors DET and the number of drive electrodes Tx.

The output data RD1, RD2, . . . , and RD6 are obtained for each selection signal SELx. The signal processing circuit 45 performs signal processing on each of the output data RD1, RD2, . . . , and Rd6 in a time-division manner to generate the image data ID. As a result, the memory 44 need not store therein the detection signals S of one frame, and the amount of data can be reduced to one-sixth of one frame. Consequently, the detecting device 1 can suppress an increase in capacity of the memory 44.

In addition, the number of data of the output data RD is reduced. Consequently, the detecting device 1 can reduce the load of signal processing performed by the signal processing circuit 45.

The method for driving the detecting device 1 described above is given by way of example only and may be appropriately modified. The number m of detection electrodes Rx is not limited to 192, for example, and may be either 191 or smaller or 193 or larger. The number n of drive electrodes Tx is not limited to 256 and may be either 255 or smaller or 257 or larger. The number k of detection electrodes Rx included in one detection electrode block RxB is not limited to 6 and may be either 5 or smaller or 7 or larger.

While the first selection circuit 15 sequentially scans the drive electrodes Tx-1 to Tx-n, the embodiment is not limited thereto. The first selection circuit 15, for example, may drive each drive electrode block composed of a plurality of drive electrodes Tx. Alternatively, the first selection circuit 15 may perform scanning by thinning out the drive electrodes Tx (skipping a plurality of drive electrodes Tx).

Modifications

Figure 11:
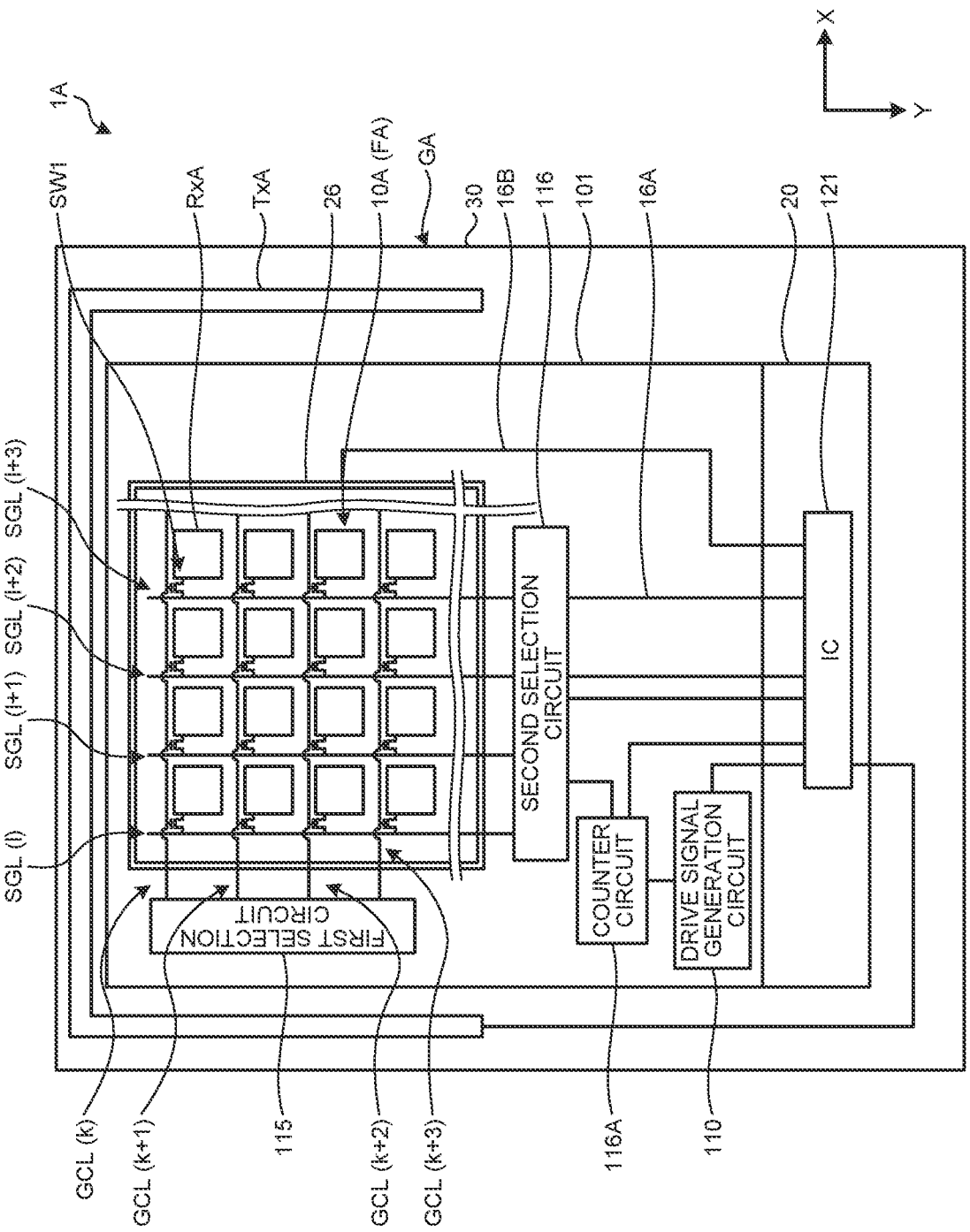
FIG. 11 is a plan view of an example of the configuration of the detecting device according to a modification.

FIG. 11 is a plan view of an example of the configuration of the detecting device according to a modification. As illustrated in FIG. 11, a detecting device 1A includes a substrate 101, a first circuit substrate 20, and a second circuit substrate 30. The substrate 101 and the first circuit substrate 20, for example, are disposed on a first surface of the second circuit substrate 30. The first circuit substrate 20 is flexible printed circuits, for example. The second circuit substrate 30 is a rigid substrate, such as a printed circuit board (PCB)), for example. The first circuit substrate 20 relays between the substrate 101 and the second circuit substrate 30.

A sensor 10A includes the insulating substrate 101, a plurality of detection electrodes RxA (detection elements SEA), a plurality of switch elements SW1, scanning lines GCL, data lines SGL, and a detection electrode TxA (drive electrode). The detection electrodes RxA are provided on a first surface of the substrate 101. The scanning lines GCL are each coupled to a plurality of switch elements SW1. The data lines SGL are each coupled to a plurality of switch elements SW1. The switch element SW1 is a thin-film transistor, for example. The scanning line GCL is wiring for supplying scanning signals to the switch elements SW1. If the switch element SW1 is a transistor, for example, the scanning line GCL is coupled to the gate of the transistor. The data line SGL is wiring electrically coupled to the detection electrodes RxA corresponding to the scanning signals received from the scanning line GCL. In other words, the data line SGL is wiring to which the detection electrodes RxA output detection signals Sv. If the switch element SW1 is a transistor, for example, the data line SGL is coupled to the source of the transistor. The substrate 101 is an insulating substrate, for example, and is made of glass material or organic material, such as polyimide.

A first selection circuit 115 and a second selection circuit 116 are provided on the first surface of the substrate 101. The data lines SGL are coupled to the second selection circuit 116. The scanning lines GCL are coupled to the first selection circuit 115.

The detection region FA is provided with the detection electrodes RxA and the switch elements SW1. If the detection region FA has a square shape, the peripheral region GA of the sensor 10A is formed along at least one side of the detection region FA. The peripheral region GA of the sensor 10A is provided with the detection electrode TxA (drive electrode). The sensor 10A further includes an electrical conductor 26. The electrical conductor 26 is disposed in the peripheral region GA. More specifically, the electrical conductor 26 is disposed between the detection electrodes RxA and the detection electrode TxA. The electrical conductor 26 is coupled to the detection circuit 40. The electrical conductor 26 is an electrode for detecting proximity of an external object (e.g., a finger) to the sensor 10A. The electrical conductor 26, for example, is coupled to a drive signal generation circuit 110 and is supplied with drive signals Vs. When a finger is in proximity to the electrical conductor 26, capacitance is generated between the electrical conductor 26 and the finger, thereby increasing the capacitance value of the electrical conductor 26. The detection circuit 40 coupled to the electrical conductor 26 detects the change in the capacitance value of the electrical conductor 26, thereby detecting proximity of the external object (e.g., a finger) to the sensor 10A. Until the detection circuit 40 detects proximity of a finger by the electrical conductor 26, the detection control circuit 11 may stop supplying the drive signals Vs to the detection electrode TxA, and the detection circuit 40 may stop receiving the detection signals Sv from the detection electrodes RxA. When the detection circuit 40 detects proximity of a finger by the electrical conductor 26, the detection control circuit 11 and the detection circuit 40 may start the operations on the detection electrode TxA and the detection electrodes RxA. The mode in which only the electrical conductor 26 operates is referred to as a standby mode.

The detection electrode TxA is supplied with the drive signals Vs. The detection electrode TxA is disposed outside the detection region FA provided with the detection electrodes RxA, for example. More specifically, the detection electrode TxA is disposed outside the electrical conductor 26. In other words, the electrical conductor 26 is disposed between the sensor 10A and the detection electrode TxA. The detection electrodes RxA, the electrical conductor 26, and the detection electrode TxA are separated from one another.

The first selection circuit 115 supplies scanning signals to the selected scanning line GCL based on the selection signals SELy supplied from the detection control circuit 11. In other words, the first selection circuit 115 selects a plurality of detection electrodes RxA (detection elements SEA) coupled to the scanning line GCL in the row direction (X-direction). The second selection circuit 116 couples the selected data line SGL to the detection circuit 40 based on the selection signals SELx supplied from the detection control circuit 11. In other words, the second selection circuit 116 selects a plurality of detection electrodes RxA (detection elements SEA) coupled to the data line SGL in the column direction (Y-direction).

As illustrated in FIG. 11, the sensor 10A includes the detection electrodes RxA, scanning lines GCL(k), GCL(k+1), GCL(k+2), and GCL(k+3), and data lines SGL(l), SGL(l+1), SGL(l+2), and SGL(l+3), for example. k and l are integers of 1 or larger. The detection electrodes RxA are arrayed in the row direction (X-direction) and the column direction (Y-direction). The scanning lines GCL(k), GCL(k+1), GCL(k+2), and GCL(k+3) are wiring for turning on and off the switch elements SW1. The scanning lines GCL(k), GCL(k+1), GCL(k+2), and GCL(k+3) are disposed side by side in the column direction (Y-direction) and extend in the row direction (X-direction). The data lines SGL(l), SGL(l+1), SGL(l+2), and SGL(l+3) are wiring for outputting the detection signals Sv. The data lines SGL(l), SGL(l+1), SGL(l+2), and SGL(l+3) are disposed side by side in the row direction (X-direction) and extend in the column direction (Y-direction). In the following description, the scanning lines GCL(k), GCL(k+1), GCL(k+2), and GCL(k+3) are simply referred to as the scanning lines GCL when they need not be distinguished from one another. The data lines SGL(l), SGL(l+1), SGL(l+2), and SGL(l+3) are simply referred to as the data lines SGL when they need not be distinguished from one another.

The first selection circuit 115 selects certain scanning lines GCL (e.g., GCL(k) and GCL(k+2)) out of the scanning lines GCL based on the selection signals SELy supplied from the detection control circuit 11. The first selection circuit 115 applies a predetermined voltage (scanning signals) to the selected scanning lines GCL(k) and GCL(k+2). As a result, the detection electrodes RxA belonging to the k-th row and the detection electrodes RxA belonging to the (k+2)-th row are coupled to the second selection circuit 116 via the data lines SGL(l), SGL(l+1), SGL(l+2), and SGL(l+3). The second selection circuit 116 selects a certain data line SGL (e.g., SGL(k)) out of the data lines SGL based on the signals supplied from the detection control circuit 11. The second selection circuit 116 couples the selected data line SGL(k) to the detection circuit 40. As a result, the detection electrode RxA in the k-th row and l-th column and the detection electrode RxA in the (k+2)-th row and l-th column supply the detection signals Sv to the detection circuit 40.

In a state where a finger is in contact with or in proximity to the sensor 10A (contact state) in the detecting device 1A according to the modification, the finger is in contact with the detection electrode TxA. The drive signals Vs supplied from the detection control circuit 11 to the detection electrode TxA affect the detection electrodes RxA via the finger and an insulating protective layer (e.g., insulating resin) that protects the sensor 10A. In other words, the finger functions as part of the detection electrode TxA. As a result, the separation distance between the detection electrode TxA and the detection electrodes RxA is substantially small in the contact state. In addition, the recesses and the protrusions of the finger are different in the distance from the detection electrodes RxA. The value of the capacitance formed at the protrusions of the finger is larger than that of the capacitance formed at the recesses of the finger. With this mechanism, the detecting device 1A enables the recesses and protrusions on the surface of the finger to be more readily reflected on a change in capacitance of the detection electrodes RxA and has higher detection sensitivity to a fingerprint than in a case where the drive signals Vs do not pass through the finger. Consequently, the detecting device 1A can improve the detection sensitivity to an external object (e.g., a finger).

As illustrated in FIG. 11, the substrate 101 is provided with the sensor 10A, the drive signal generation circuit 110, and a counter circuit 116A, for example. Each detection electrode RxA included in the sensor 10A is coupled to the first selection circuit 115 via one corresponding scanning line GCL. Each detection electrode RxA included in the sensor 10A is also coupled to the input stage of the second selection circuit 116 via one corresponding data line SGL. The counter circuit 116A is coupled to the first selection circuit 115, the second selection circuit 16, and the drive signal generation circuit 110 via wiring. The first selection circuit 115 is disposed between the detection electrodes RxA and the detection electrode TxA. The electrical conductor 26 is disposed between the first selection circuit 115 and the detection electrodes RxA.

The first circuit substrate 20 is provided with an IC 121. The output stage of the second selection circuit 116 is coupled to a plurality of terminals of the IC 121 via a plurality of wires 16A. The electrical conductor 26 is coupled to one terminal of the IC 121 via wiring 16B. The counter circuit 116A is coupled to the IC 121 via wiring. The drive signal generation circuit 110 is coupled to the IC 121 via wiring.

The detection electrode TxA is disposed on the first surface of the second circuit substrate 30. The drive signal generation circuit 110 is coupled to the detection electrode TxA via the IC 121 and the wiring on the second circuit substrate 30. The detection electrode TxA may have a ring shape surrounding the sensor 10A or a shape obtained by removing part of the ring surrounding the sensor 10A as illustrated in FIG. 11. The detection electrode TxA may have a shape obtained by removing one of the four sides in a square ring surrounding the sensor 10A, for example. The detection electrode TxA, for example, may be disposed in a manner not overlapping the data lines SGL that couple the sensor 10A to the second selection circuit 116 in planar view. The detection electrode TxA may be disposed in a manner not overlapping the wires 16A that couple the second selection circuit 116 to the IC 121 in planar view. This configuration can prevent the drive signals Vs supplied to the detection electrode TxA from affecting the data lines SGL or the wires 16A as noise.

At least part of the configuration of the detection control circuit 11 and at least part of the configuration of the detection circuit 40 illustrated in FIG. 1 are included in the IC 121. The detection signal amplification circuit 42, the A/D conversion circuit 43, the memory 44, the signal processing circuit 45, the communication circuit 46, and the detection timing control circuit 47 out of the various components of the detection circuit 40 illustrated in FIG. 1, for example, are included in the IC 121. At least part of the circuits out of the various components of the detection control circuit 11 illustrated in FIG. 1 are included in the IC 121. At least part of the configuration of the detection circuit 40 illustrated in FIG. 1 are formed on the substrate 101. The counter circuit 116A and the drive signal generation circuit 110 out of the various components of the detection control circuit 11 illustrated in FIG. 1, for example, are formed on the substrate 101. The IC 121 may include a protective circuit as a circuit coupled to the drive signal generation circuit 110 and the detection electrode TxA. The protective circuit is a diode, for example, and prevents electro-static discharge (ESD) from being transmitted from the detection electrode TxA to the sensor 10A via the IC 121.

At least part of the configuration of the detection control circuit 11 illustrated in FIG. 1 may be included in the first selection circuit 115. At least part of the configuration of the detection control circuit 11 or at least part of the configuration of the detection circuit 40 illustrated in FIG. 1 may be included in an IC disposed on the second circuit substrate 30 separately from the IC 121. The protective circuit, for example, may be provided on the second circuit substrate 30 and be coupled to the drive signal generation circuit 110 and the detection electrode TxA not via the IC 121. At least part of the configuration of the detection control circuit 11 and the detection circuit 40 may be included in a central processing unit (CPU) disposed on an external substrate coupled to the second circuit substrate 30. The substrate 101 may include an integrated circuit, which is not illustrated. In this case, at least part of the configuration of the detection control circuit 11 and at least part of the configuration of the detection circuit 40 illustrated in FIG. 1 may be included in the integrated circuit of the substrate 101. The detection signal amplification circuit 42 out of the various components of the detection circuit 40, for example, may be included in the integrated circuit of the substrate 101.

While exemplary embodiments according to the present disclosure have been described, the embodiments are not intended to limit the disclosure. The contents disclosed in the embodiments are given by way of example only, and various modifications may be made without departing from the spirit of the present disclosure. Appropriate modifications made without departing from the spirit of the present disclosure naturally fall within the technical scope of the disclosure.

What is claimed is:

1. A detecting device comprising:
   a substrate;
   a plurality of detection electrodes provided on the substrate and arrayed in a first direction parallel to the substrate;
   a plurality of drive electrodes provided on the substrate and arrayed in a second direction intersecting the first direction;
   a second selection circuit configured to select a plurality of the detection electrodes based on selection signals;
   a first selection circuit configured to select a plurality of the drive electrodes;
   a detector coupled to the selected detection electrodes out of the detection electrodes; and
   a memory storing therein, as a set of output data, a plurality of detection signals output from the selected detection electrodes via the detector by the first selection circuit scanning the drive electrodes in one period when the second selection circuit selects the detection electrodes.

2. The detecting device according to claim 1, wherein the memory stores therein the detection signals output due to each of the different selection signals as different pieces of the output data.

3. The detecting device according to claim 1, further comprising:
   a signal processing circuit configured to receive the output data stored in the memory and perform signal processing on the detection signals, wherein
   the different pieces of the output data are stored in a time-division manner in a period for performing detection of one frame, and a period in which the output data is stored and a period in which the signal processing circuit performs the signal processing are alternately arranged.

4. The detecting device according to claim 1, further comprising
   a plurality of detection electrode blocks each composed of a plurality of the detection electrodes, wherein
   the second selection circuit selects a first detection electrode from each of the detection electrode blocks based on a first selection signal, and the first selection circuit scans the drive electrodes in a period when the first selection signal is at a high-level voltage, and
   the second selection circuit selects a second detection electrode from each of the detection electrode blocks based on a second selection signal, and the first selection circuit scans the drive electrodes in a period when the second selection signal is at a high-level voltage.

5. The detecting device according to claim 4, further comprising
   a plurality of the detectors, wherein
   the detectors are provided corresponding to the respective detection electrode blocks, and
   number of the detection signals included in the set of output data is a product of number of the detectors and number of the drive electrodes.

6. The detecting device according to claim 1, wherein
   the detection electrodes each include a plurality of first linear parts, a plurality of second linear parts extending in a direction intersecting the first linear parts, and a bent part coupling the first linear part and the second linear part,
   the first linear parts and the second linear parts are metal thin wires, and
   the drive electrodes are translucent electrical conductors.

* * * * *